Figure 1:
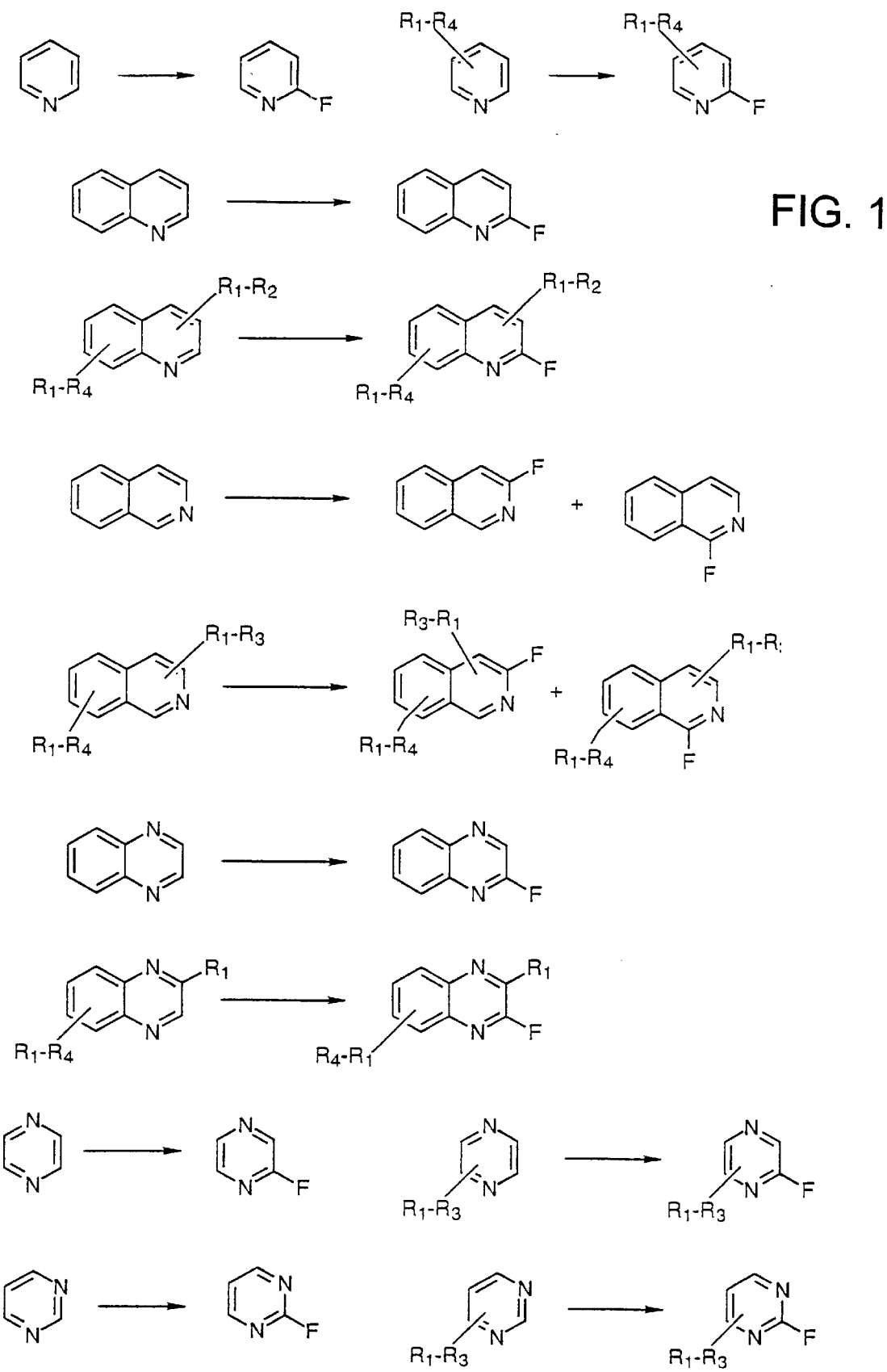

United States Patent [19]
Chambers et al.

[11] Patent Number: 5,859,255
[45] Date of Patent: Jan. 12, 1999

[54] PROCESS FOR THE PREPARATION OF FLUORINATED HETEROCYCLIC COMPOUNDS

[75] Inventors: Richard Dickinson Chambers, Whitesmocks; Graham Sandford, Gilesgate, both of England

[73] Assignee: F2 Chemicals Ltd., Lancashire, United Kingdom

[21] Appl. No.: 849,942

[22] PCT Filed: Dec. 18, 1995

[86] PCT No.: PCT/GB95/02950

§ 371 Date: Jun. 20, 1997

§ 102(e) Date: Jun. 20, 1997

[87] PCT Pub. No.: WO96/19456

PCT Pub. Date: Jun. 27, 1996

[30] Foreign Application Priority Data

Dec. 21, 1994 [GB] United Kingdom .................. 9425796

[51] Int. Cl.[6] ..................... C07D 211/72; C07D 211/84; C07D 213/61; C07D 221/12
[52] U.S. Cl. .................... 546/345; 546/108; 546/122; 546/180
[58] Field of Search ...................... 546/345, 180, 546/108, 122

[56] References Cited

U.S. PATENT DOCUMENTS

| 2,013,030 | 9/1935 | Calcott | 552/263 |
| 4,786,733 | 11/1988 | Van Der Puy | 546/286 |
| 5,455,373 | 10/1995 | Kawa | 560/300 |

OTHER PUBLICATIONS

Chemical Abstracts #124:55893, abstract of Tetrahedron Lett, vol.36(37), pp. 6705–6708, 1995.
Chemical Abstracts #110:154118, abstract of J Org Chem, vol. 54(7), pp. 1726–1731, 1989.
Chemical Abstracts #116:234035, abstract of EP 499930, 1992.
March J., *Advanced Organic Chemistry,* John Wiley & Sons, New York (1992), pp. 534 & 671.
Rozen et al., A Novel Aromatic Iodination Method Using $F_2$, Journal of Organic Chemistry 55:3552–3555 (1990).

*Primary Examiner*—John Kight
*Assistant Examiner*—D. Margaret M. Mach
*Attorney, Agent, or Firm*—Klarquist Sparkman Campbell Leigh & Whinston, LLP

[57] ABSTRACT

A method of fluorinating a heterocyclic organic compound comprises the step of reacting a heterocyclic compound with elemental fluorine in the presence of another halogen. The reaction may be conducted in the presence of a base.

16 Claims, 2 Drawing Sheets

PROCESS FOR THE PREPARATION OF FLUORINATED HETEROCYCLIC COMPOUNDS

The present invention relates to the preparation of halogenated compounds, in particular, halogenated heterocyclic compounds. More particularly, the invention relates to the fluorination of heterocyclic compounds.

The preparation of halogenated heterocycles has received a great deal of attention due to the many synthetic and industrial processes in which such substrates are employed, for example, in the pharmaceutical, plant protection and dye industries.

Few methods are available for the introduction of a fluorine atom at the 2- and/or 6-positions of pyridine. Traditionally, routes to 2-fluoropyridines have been based on multi-step BalzSchieman type decompositions of pyridine diazonium tetrafluoroborate salts. Halogen exchange processes involving the reaction of a fluoride ion source, such as $SbF_5$, KF, HF, etc, with a chlorinated pyridine at elevated temperatures have frequently been used to prepare fluoropyridines. The electrochemical fluorination of pyridine in the presence of a source of fluoride ion gave 2-fluoropyridine in only 22% yield. With xenon difluoride, pyridine gave a mixture of fluoropyridines and, also, cesium fluorooxysulfate reacts with pyridine at room temperature in ether to give 2-fluoropyridine in 61% yield.

The preparation of related fluorine-containing heterocycles such as 2-fluoroquinoline may be accomplished by similar methodology, ie halogen exchange processes, fluorodediazotisation. etc.

A method for the direct fluorination of organic compounds is disclosed in U.S. Pat. No. 2013030. However, the technique is primarily directed towards non-heterocyclic derivatives and, in any event, is subject to unwanted side reactions and, as a consequence, yields of desired products are generally poor, and the material obtained is in a low state of purity. Preparations of 2-fluoropyridines by direct reaction with elemental fluorine have also been reported in U.S. Pat. No. 4786733. In this case, the reactions are kinetically competitive with side chain fluorination and, therefore, yields of the desired 2-fluoropyridines are again low. In addition, the reported reaction of elemental fluorine with quinoline results in predominant fluorination of the annulated aromatic ring and extensive fragmentation of the hetero ring. Surprisingly, it has now been found that heterocyclic compounds can be selectively fluorinated by elemental fluorine when another halogen is present in the reaction medium.

According to the present invention, there is provided a method of preparing a heterocyclic organic compound having at least one fluorine substituent in the heterocyclic ring, the method comprising the step of reacting a heterocyclic compound with elemental fluorine in the presence of at least one of chlorine, bromine, iodine and an interhalogen compound.

Examples of interhalogen compounds are iodine monobromide and iodine monochloride.

The heterocyclic compound which is fluorinated by the method of the present invention may be a nitrogen-containing heterocyclic compound. The heterocyclic compound may include a five- or six-membered ring which may contain optional sustituents. The ring may be attached or fused to another one or more rings which may or may not be heterocyclic.

The heterocyclic compound preferably includes a six-membered aromatic ring containing one or more nitrogen atoms such as pyridine or a related heterocycle such as pyrimidine, pyridazine or triazine, or a related benzo-fused heterocycle such as quinoline, isoquinoline, quinoxaline or quinoazoline, or a bi-or poly-cyclic compound such as bipyridine.

The positions of the ring or rings of the heterocyclic compound fluorinated by the method according to the present invention which are not occupied by heteroatoms may carry substituents. Thus, where the heterocycle is pyridine it may carry substituents at from one to five ring positions. Where the heterocycle is a pyrimidine it may carry substituents at from one to four ring positions. Where the heterocycle is quinoline or isoquinoline it may carry substituents at from one to six ring positions. Optional ring substituents (which may themselves contain optional substituents) may be independently selected from alkyl, alkoxy, halogen, —CN, —OH, —NO$_2$, —NH$_2$, NHalkyl, —N(alkyl)$_2$, —NHCOalkyl, —COOalkyl, —COOH, —COalkyl, —CONH$_2$, —CONH(alkyl), —CON(alkyl)$_2$, —COY, —CY$_3^1$ and SO$_2$Y$^2$ wherein Y is —H, —F, —Cl, —Br, alkyl, —OH or —Oalkyl Y$^1$ is —F or —Cl Y$^2$ is —F, —Cl, —Br, —NH$_2$, —NHalkyl, or —N(alkyl)$_2$.

In each of these substituents alkyl is preferably $C_{1-4}$-alkyl, alkoxy is preferably $C_{1-4}$-alkoxy and halogen is preferably —F or —Cl.

In each of these substituents alkyl is preferably $C_{1-4}$-alkyl, alkoxy is preferably $C_{1-4}$-alkoxy and halogen is preferably —F or —Cl.

When the aromatic compound is pyridine, it is preferably unsubstituted, monosubstituted or disubstituted. When pyridine is monosubstituted, it is preferably substituted in the 4-position. When pyridine is disubstituted, it is preferably substituted in the 2- and 4-position.

Preferred substituents for the heterocyclic compound are selected from —OH, —CN, —NO$_2$, NHCOCH$_3$, —OCH$_3$, —COOCH$_3$, —COOH, —COCH$_3$, —CH$_3$, —F, —Cl, —Br, —CF$_3$ and —CONH$_2$ and combinations thereof.

All hydrogens on carbon atoms bonded to the heteroatom may be substituted by fluorine if the stoichiometry of the experiment is altered. For instance, two fluorine atoms may be selectively introduced into heterocyclics as, for instance, pyridine gave 2,6-difluoropyridine when two equivalents each of fluorine and, halogen were used. By a similar process, quinoxaline gave 2,3-difluoroquinoxaline and pyrimidine gave difluorinated pyrimidines.

In a preferred method according to the present invention, a base is added to the reaction medium. The base may be an organic base such as triethylamine or an inorganic base such as sodium fluoride. It has been surprisingly found that this addition of a base to the reaction medium gives a significantly higher conversion of starting heterocyclic to fluorinated products in a given time.

Examples of fluorinations which may be carried out by the method of the present invention are given in FIG. 1 of the accompanying drawings. The groups $R_1$ to $R_4$ are independently selected from hydrogen and the various substituents for hydrogen specified above.

Figure 2:
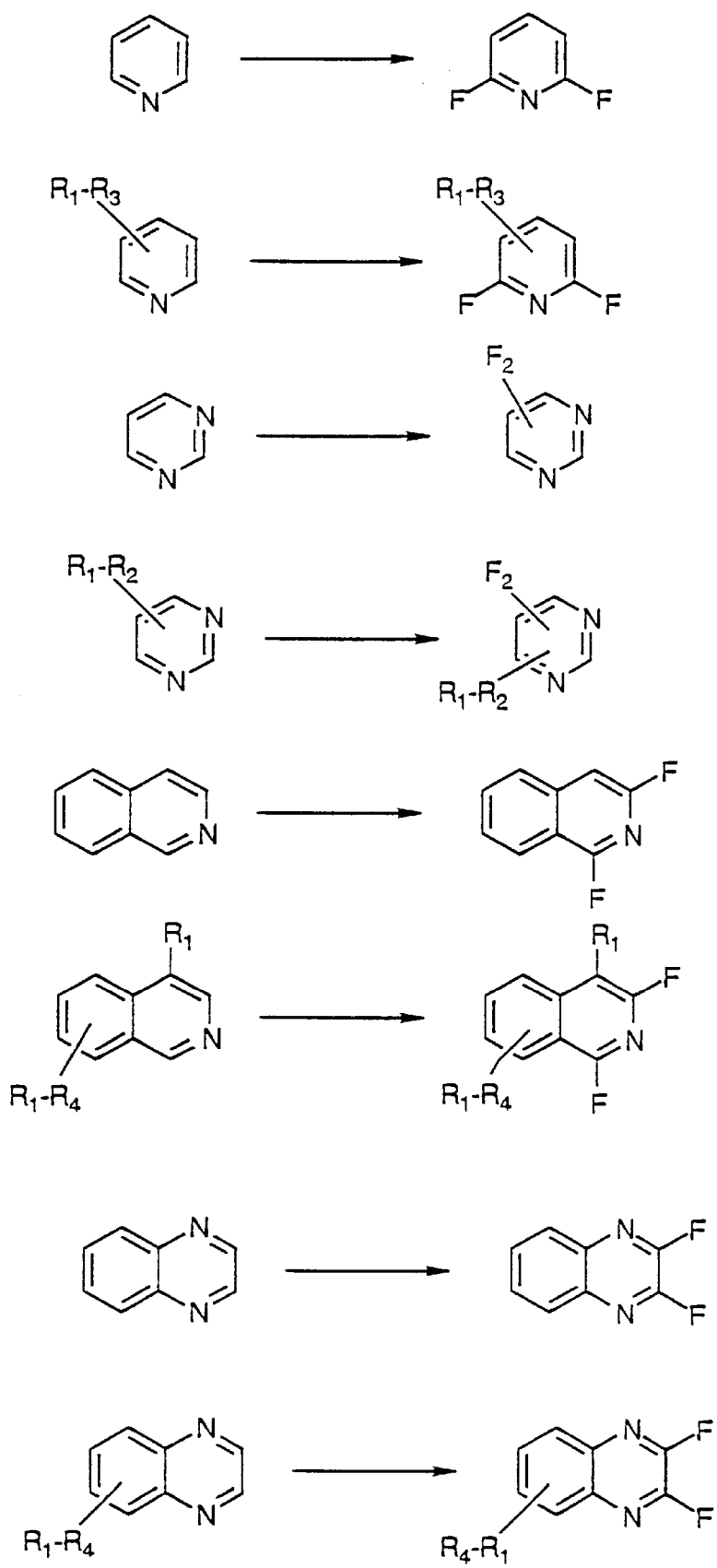

FIG. 2 of the accompanying drawings gives examples of fluorinations by the method of the present invention in which two fluorine atoms are introduced into the heterocycle. Again the groups are $R_1$ to $R_4$ are independently selected from hydrogen and the various substituents for hydrogen specified above.

Examples of organic bases which may be used are triethylamine, tributylamine and N-methylpiperidine. Examples of inorganic bases are sodium fluoride and potassium fluoride.

The ratio of base to the heterocyclic compound may be varied within wide limits although it is preferred that the molar ratio is in the range 0.2 to 8.0:1, especially 1.0 to 1.4:(base: heterocyclic compound).

The method according to the present invention may be carried out by passing fluorine gas into a liquid which contains the heterocyclic compound, halogen and, if used, base. The reaction may be carried out in the vessel in which the liquid is present or alternatively a flow-stream of the liquid may be contacted with the gaseous flow of fluorine in countercurrent fashion. The liquid may comprise a common inert, organic solvent such as acetonitrile or a fluorinated organic liquid such as a fluorinated alkane (eg $CF_2ClCFCl_2$), a perfluoroalkane, perfluorodecalin, a fluorinated ether, a perfluorinated ether, or a partly fluorinated alkane.

The process may be carried out at a temperature from −20° C. to 80° C., preferably at a temperature from −10° C. to 30° C. and especially at a temperature from −5° C. to 25° C.

The fluorine gas is preferably diluted before use by mixing with an inert gas such as nitrogen or helium. The concentration of fluorine is preferably from 1% to 50% by volume, more preferably from 2% to 25% and especially from 5% to 15%.

The ratio of fluorine to heterocyclic compound may be varied within wide limits although it is preferred that the molar ratio of fluorine to aromatic compound is from 0.5:1 to 6:1 and especially from 1:1 to 4:1. Use of a higher ratio for fluorine to heterocyclic compound ensures that more than one fluorine atom can be selectively introduced into the heterocyclic compound.

When fluorination is complete, the fluorinated products may be isolated by purging the reaction mixture with nitrogen to remove any residual fluorine gas, followed by dilution with excess water and neutralisation, followed by extraction into a suitable solvent, followed by distillation. The fluorinated heterocyclic products may be separated by fractional distillation, chromatography or by crystallisation from a suitable solvent.

When fluorination is complete, the fluorinated products may be isolated by purging the reaction mixture with nitrogen to remove any residual fluorine gas, followed by dilution with excess water and neutralisation, followed by extraction into a suitable solvent, followed by distillation. The fluorinated heterocyclic products may be separated by fractional distillation, chromatography or by crystallisation from a suitable solvent.

The method according to the present invention offers a simple, convenient route to the preparation of fluorinated heterocycles directly from the parent heterocycle and elemental fluorine. Thus, the preparation of chlorinated heterocycles for halogen exchange reactions or aminated heterocycles for dediazotisation reactions is not necessary in the method of the present invention. Thus, the present method offers a simple one-step procedure for the preparation of fluorinated heterocycles.

The introduction of a base into the reaction mixture ensures rapid conversion of starting material to product and is, therefore, a particularly advantageous embodiment of the present invention.

The method according to the present invention is further illustrated with reference to the following examples:

Example 1: Preparation of 2-fluoropyridine

A solution containing pyridine (9.5 g, 120 mmol) and iodine (30.0 g, 118 mmol) in Arklone (Trade Mark) ($CFCl_2$—$CFCl_2$) (150 ml) was placed in a fluorination apparatus fitted with a drying tube filled with soda lime. Elemental fluorine (165 mmol) as a 10% mixture in dry nitrogen was then passed through the stirred solution using narrow bore PTFE tubing at ca. 40 ml/min. After the fluorine had been added, the solution was poured into 10% aqueous sodium metabisulfite solution (300 ml), neutralised with solid sodium bicarbonate and continuously extracted with dichloromethane. The organic extracts were dried and evaporated to a yellow oil which was identified as 2-fluoropyridine (6.5 g, 56%) in >95% purity by GC; ($\delta_H$(200 MHz, $CDCl_3$, $Me_4Sl$) 6.9 ppm (1H, m), 7.2 (1H, m), 7.8 (1H, m), 8.2 (1H, m); (C (50 MHz, $CDCl_3$, $Me_4Si$) 109.4 ppm (d, $^2J_{C-F}$ 37.1, 3-C), 121.3 (d, $^4J_{C-F}$4.2, 5-C), 141.2(d, $^3J_{C-F}$ 7.7, 4-C), 147.5 (d, $^2J_{C-F}$14.5, 6-C), 163.5 (d, $^1J_{C-F}$237.4, 2-C); ($\delta_F$ (235 MHz, $CDCl_3$, $CFCl_3$)−67.9 ppm (s, 2-F); m/z (E1+) 97 ($M^+$, 100%), 70 (68), 69 (12), 57 (18), 50 (29), 39 (22).

Example 2: Preparation of 4.7-dichloroquinoline without use of base

A solution containing 4,7-dichloroquinoline (1.0 g, 5 mmol) and iodine (1.28 g, 5 mmol) in $CF_2ClCFCl_2$(30 ml) was placed in a fluorination apparatus fitted with a drying tube filled with soda lime. Elemental fluorine (7 mmol) as a 10% mixture by volume in dry nitrogen was then passed through the stirred solution using narrow bore PTFE tubing at ca. 15 ml/min. After the fluorine had been added, the solution was poured into 10% aqueous sodium metabisulfite solution (30 ml) and extracted with dichloromethane. The organic extracts were dried and evaporated to an oil (0.98 g). GC/MS analysis showed a 34% conversion of starting material. Column chromatography on silica gel with dichloromethane as eluant gave 2-fluoro-4,7-dichloroquinoline (0.33 g, 87%) as white crystals; other data were the same as that described in the following reaction.

Example 3: Fluorination of 4.7-dichloroquinoline with use of base

A solution containing 4,7-dichloroquinoline (1.0 g, 5 mmol), iodine (1.28 g, 5 mmol) and triethylamine (0.51 g, 5.1 mmol) in $CF_2ClCFCl_2$(30 ml) was placed in a fluorination apparatus fitted with a drying tube filled with soda lime. Elemental fluorine (7 mmol) as a 10% mixture in dry nitrogen was then passed through the stirred solution using narrow bore PTFE tubing at ca. 15 ml/min. After the fluorine had been added, the solution was poured into 10% aqueous sodium metabisulfite solution (30 ml) and extracted with dichloromethane. The organic extracts were dried and evaporated to a brown oil (1.06 g). GC/MS analysis showed a 69% conversion of starting material. Column chromatography on silica gel with dichloromethane as eluant gave 2-fluoro-4,7-dichloroquinoline (0.66 g, 88%) as white crystals; m.p. 105°–106° C. (vacuum sublimation oil bath temp. 60° C./<1 mmHg); $R_F$ 0.72; (Found: C, 49.7; H, 1.7;N, 6.3. $C_9H_4Cl_2FN$ requires: C, 50.0; H, 1.85; N, 6.5%); $\delta_H$ (400 MHz; $CDCl_3$; $Me_4Si$) 7.20 ppm (1H, d, $J_{H3,F}$2.4,H-3),7.58 (1H, d d, $J_{H5,H6}$,9.0 $J_{H6,H8}$2.2, H-6), 7.95 (1H, d, $J_{H6,H8}$2.0, H-8), 8.13 (1H, d, $J_{H5,H6}$9.2, H-5); $\delta F$ (235MHz; $CDCl_3$; $Me_4Si$)−60.0ppm (s); $\delta_C$(100 MHz, $CDCl_3$, $Me_4Si$)110.38 (d, $^2J$ 45.8, C-3), 123.6 (d,$^4J$ 2.3, C-4a), 125.5 (s, C-6), 127.6 (d, $^5J$ 1.2, C-5), 128.1 (d, $^4J$ 2.6, C-8), 137.9 (s, C-7), 146.4 (d, $^3J$ 24.6, C-4), 146.6 (d, $^3J$ 18.5, C-8a), 160.9 (d, $^1J$ 244.1, C-2); m/z (E1+) 215 ($M^+$, 100%), 217 (61, $M^+$+2), 219 (11, $M^{30}$ +4), 182(14), 180 (40), 145 (18).

Example 4: Fluorination of 3-bromoquinoline with use of base

A solution containing 3-bromoquinoline (1.0 g, 4.8mmol), iodine (1.22g, 4.8mmol) and triethylamine (0.48 g, 4.8 mmol) in $CF_2ClCFCl_2$ (30 ml) was placed in a fluorination apparatus fitted with a drying tube filled with soda lime. Elemental fluorine (5 mmol) as a 10% mixture in dry nitrogen was then passed through the stirred solution using narrow bore PTFE tubing at ca. 15 ml/min. After the fluorine had been added the solution was poured into 10% aqueous sodium metabisulfite solution (30 ml) and extracted with dichloromethane. The organic extracts were dried and evaporated to a brown oil (0.95 g). GC/MS analysis showed a 56% conversion of starting material. Column chromatography on silica gel with dichloromethane as eluant gave 2fluoro-3-bromoquinoline (0.52g, 85%); mp 75°–76° C. (vacuum sublimation oil bath temp. 50° C./<1 mmHg) as white needles; $R_F$ 0.69 ($CH_2Cl_2$); (Found: C, 47.5; H, 2.1; N, 6.2. $C_9H_5NBrF$ requires: C, 47.8; H, 2.2; N, 6.2%); $\delta_H$ (400 MHz, $CDCl_3$, $Me_4Si$) 7.55 ppm (1H, d d, $J_{H5,H6}=J_{H6,H7}$ 8.0, H-6), 7.74 (1H, d d d, $J_{H7,H8}$ 8.4, $J_{H6,H7}$ 7.2, $J_{H5,H7}$ 1.2, H-7), 7.76 (1H,d, $J_{H5,H6}$ 8.0, H-5), 7.91 (1H, d d, $J_{H7,H8}$ 8.4, $J_{H6,H8}$ 0.8, H-8), 8.42 (1H, d, $J_{H4,F}$ 8.4, H-4); $\delta_C$ (100 MHz, $CDCl_3$, $Me_4Si$) 104.0 (d, $^2J$ 43.2, C-3), 126.6 (s, C-6), 127.0 (d, $^4J$ 2.7, C-8), 128.0 (d, $^5J$ 1.9, C-5) 128.0 (d, $^4J$ 2.2, C-4a), 130.9 (d, $^5J$ 1.1, C-7), 143.5 (d, $^3J$, 3.7, C-4), 144.2 (d, $^3J$ 15.1, C-8a), 157.3 (d, $^1J$ 238.1, C-2); $\delta_F$ (235 MHz, $CDCl_3$, $CFCl_3$) −60.8ppm (s); m/z (E1+) 225 ($M^+$, 100%), 227 ($M^+$, 74), 146 (56), 126 (23), 101 (18), 75 (14).

Example 5: Fluorination of 4-Chloroquinoline

A solution containing 4-chloroquinoline (1.0 g, 6 mmol), iodine (1.55 g, 6 mmol) and triethylamine (0.60 g, 6 mmol) in $CF_2ClCFl_2$ (30 ml) was placed in a fluorination apparatus fitted with a drying tube filled with soda lime. Elemental fluorine (7 mmol) as a 10% mixture in dry nitrogen was then passed through the stirred solution at room temperature using narrow bore PTFE tubing at 20 ml/min. After the fluorine had been added the solution was poured into 10% aqueous sodium metabisulfite solution (30 ml) and extracted with dichloromethane. The organic extracts were dried and evaporated to a brown oil (1.01 g). GC/MS analysis showed a 76% conversion of starting material. Column chromatography on silica gel with dichloromethane as eluant gave 2 fluoro-4-chloroquinoline (0.76 g, 90%); m.p 60°–61° C. (vacuum sublimation oil bath temp. 50° C./<1 mmHg) as white needles; $R_F$ 0.78 ($CH_2Cl_2$); (Found C, 59.7;H, 2.9; N, 7.6. $C_9H_5NClF$ requires: C, 59.5; H, 2.75; N, 7.7%); $\delta_H$ (400 MHZ, $CDCl_3$, $Me_4Si$) 7.20 ppm (1H, d, $J_{H3,F}$ 2.4, H-3), 7.62 (1H, d d d, $J_{H5,H6}=J_{H6,H7}$ 7.4, $J_{H6,H8}$ 1.2, H-6), 7.78 (1H, d d d, $J_{H6,H7}=J_{H7,H8}$ 7.8, $J_{H5,H7}$ 1.2, H-7), 7.96 (1H, d, $J_{H7,H8}$ 8.4, H-8), 8.19 (1H, d, $H_{H5,H6}$ 8.4, H-5); $\delta_F$ (235 MHz, $CDCl_3$, $CFCl_3$) −61.5 pm (s); $\delta_C$ (100 MHz, $CDCl_3$, $Me_4Si$) 110.2 ppm (d, $^2J$ 45.8, C-3), 124.2 (d, $^5J$ 0.8, C-5), 125.1 (d,$^4J$ 2.6, C-4a), 127.0 (d $^6J$ 2.7, C-6), 128.5 (d, $^4J$ 1.5, C-8), 131.6 (s, C-7), 145.9 (d, $^3J$ 18, C-8a), 146.6 (d, $^3J$ 12.5, C-4), 160.2 (d, $^1J$ 242.3, C-2); m/z ($E1^+$) 183 ($M^+$, 26%), 181 ($M^+$, 100%), 146 (35), 126 (15), 75 (12), 50 (11).

Example 6: Fluorination of 6-Chloroquinoline

A solution containing 6-chloroquinoline (1.0 g, 6.1 mmol), iodine (1.55 g, 6.1 mmol) and triethylamine (0.62 g, 6.2 mmol) in $CF_2ClCFCl_2$ (30 ml) was placed in a fluorination apparatus fitted with a drying tube filled with soda lime. Elemental fluorine (7 mmol) as a 10% mixture in dry nitrogen was then passed through the stirred solution using narrow bore PTFE tubing at ca. 15 ml/min. After the fluorine had been added the solution was poured into 10% aqueous sodium metabisulfite solution (30 ml) and extracted with dichloromethane. The organic extracts were dried and evaporated to a brown solid (1.03 g). GC/MS analysis showed a 79% conversion of starting material. Column chromatography on silica gel with dichloromethane as eluant gave 2-fluoro-6-chloroquinoline (0.82 g, 93%), $R_F$ 0.78 ($CH_2Cl_2$); $\delta_H$ (400 MHz $CDCl_3$, $Me_4Si$) 7.12 ppm (1H, d d, $J_{H3,H4}$ 8.8, $J_{H3,F}$ 2.8, H-3), 7.67 (1H, d d, $J_{H7,H8}$ 9.2, $J_{H5,H7}$ 2.4, H-7), 7.82 (1H, d, $J_{H5,H7}$ 2.4, H-5), 7.87 (1H, d, $J_{H7,H8}$ 9.0, H-8), 8.16 (1H, d d, $J_{H3,H4}=J_{H4,F}$ 8.8, H-4);$\delta_C$ (100 MHz, $CDCl_3$, $Me_4Si$) 111.1 ppm (d, $^2J$ 42.3, C-3), 126.3 (s, C-5), 127.3 (s, C-4a), 129.6 (s, C-8), 131.4 (s, C-7), 131.9 (s, C-6) 141.0 (d,$^3J$ 9.9, C-4), 144.1 (d $^3J$ 16.8, C-8a), 161.2 (d, $^1J$ 243.8, C-2); $\delta_F$ (235 MHz, $CDCl_3$, $CFCl_3$) −61.5 ppm (s); m/z (E1+) 181 ($M^+$, 100%), 183 ($M^+$, 32), 146 (34), 126 (11).

Example 7: Fluorination of Phenanthridine with use of base

A solution containing phenanthridine (1.0 g, 5.6 mmol), iodine (1.4 g, 5.6 mmol) and triethylamine (0.56 g, 5.6 mmol) in $CF_2ClCFCl_2$ (30 ml) was placed in a fluorination apparatus fitted with a drying tube filled with soda lime. Elemental fluorine (7 mmol) as a 10% mixture in dry nitrogen was then passed through the stirred solution using narrow bore PTFE tubing at ca. 15 ml/min. After the fluorine had been added the solution was poured into 10% aqueous sodium metabisulfite solution (30 ml) and extracted with dichloromethane. The organic extracts were dried and evaporated to a brown oil (0.92 g). GC/MS analysis showed a 53% conversion of starting material. Column chromatography on silica gel with dichloromethane as eluant gave 6-fluoro-phenanthridine (0.39 g, 67%), $R_F$ 0.78 ($CH_2Cl_2$); $\delta_H$ (400 MHz, $CDCl_3$, $Me_4Si$) 7.61 ppm (1H, d d d, $J_{H1,H2}=J_{H2,H3}$=7.8, $J_{H2,H4}$ 1.2, H-2), 7.69 (2H, m, H-3 and H-9), 7.88 (1H, d d d, $J_{H7,H8}$ 8.4, $J_{H8,H9}$ 7.2, $J_{H8,H10}$ 1.4, H-8), 7.97 (1H, d d, $J_{H3,H4}$ 8.0, $J_{H2,H4}$ 1.2, H-4), 8.21 (1H, d d, $J_{H9,H10}$ 8.0, $J_{H8,H10}$ 1.4, H-10) 8.45 (1H, d d, $J_{H1,H2}$ 8.0, $J_{H1,H3}$ 0.8, H-1), 8.52 (1H, d d, $J_{H7,H8}$ 8.4 $J_{H7,H9}$ 1.2, H-7); $\delta_F$ (376 MHz, $CDCl_3$, $CFCl_3$), 68.2 ppm (s); $\delta_C$ (100 MHz, $CDCl_3$, $Me_4Si$) 117.3 ppm (d, $^2J$ 35.1, C-6a), 122.2 (d, $^3J$ 3.8, C-7), 122.2 (s, C-1), 123.9 (d, $^4J$ 1.9, C-10b), 124.2 (s, C-10), 126.5, (d, $^6J$ 2.3, C-2), 127.9 (s, C-9), 128.7 (d, $^4J$ 1.6, C-4), 129.4 (s, C-3), 132.1 (s, C8), 136.5 (d, $^3J$ 7.2, C-10a), 141.5 (d, $^3J$ 17.9, C-4a), 158.1 (d, $^1J$ 248.7, C-6); m/z ($E1^+$) 197 ($M^+$, 100%).

Example 8: Fluorination of 4-ethyl-pyridine

A solution containing 4-ethylpyridine (12.8 g, 120 mmol) and iodine (30.5 g, 120 mmol) in $CF_2ClCFCl_2$ (150 ml) was placed in a fluorination apparatus fitted with a drying tube filled with soda lime. Elemental fluorine (165 mmol) as a 10% mixture in dry nitrogen was then passed through the stirred solution using narrow bore PTFE tubing at ca. 40 ml/min. After the fluorine had been added the solution was poured into 10% aqueous sodium metabisulfite solution (300 ml), neutralised with solid sodium bicarbonate and extracted with dichloromethane. The organic extracts were dried and evaporated to a yellow oil (9.54 g) which contained ethlpyridine (78 % conversion), 2-fluoropyridine and other minor products by GC/MS. The oil redissolved in dichloromethane and washed with 2N HCl solution, dried ($MgSO_4$) and evaporated to a clear oil to give 2-fluoro-4-ethylpyridine in >95% purity (6.3 g, 54% based on 78% conversion); $\delta_H$ (200 MHz, $CDCl_3$, $Me_4Si$) 1.26 ppm (3H, t, J 7.6, $CH_3$), 2.69 (2H, q, J 7.6, $CH_2$), 6.75 (1H, s, H-3), 7.02 (1H, d m, J 5.1, H-5), 8.09 (1H, d, J 5.1, H-6); $\delta_C$ (50 MHz, $CDCl_3$, $Me_4Si$) 14.1 ppm (s, $CH_3$), 28.2 (d, $^4JC-F$ 2.7, CH$_2$), 108.5 (d, $^2$J$_{C-F}$ 36.5, C-3), 121.3 (d, $^4$J$_{C-F}$ 3.9, C-5), 147.3 (d, $^3$J$_{C-F}$ 15.2, C-6), 159.3 (d, $^3$J$_{C-F}$ 7.8, C-4), 164.2 (d, $^1$J$_{C-F}$ 236.3, C-2); δ$_F$ (235 MHz, CDCl$_3$, CFCl$_3$) 69.9 ppm (s); m/z (E1+125 (M$^+$, 100%), 110 (47), 97 (15), 83 (13).

Example 9: Fluorination of quinoline

A solution containing quinoline (10.6 g, 82.5 mmol) and iodine (21.0 g, 82.5 mmol) in CF$_2$ClCFCl$_2$ (150 ml) was placed in a fluorination apparatus fitted with a drying tube filled with soda lime. Elemental fluorine (165 mmol) as a 10% mixture in nitrogen was then passed through the stirred solution using a narrow bore PTFE tubing at ca. 40 ml min$^{-1}$. After the fluorine had been added the solution was poured into aqueous sodium metabisulphite solution (300 ml), neutralised with sodium bicarbonate and extracted with dichloromethane. The organic extracts were dried (MgSO$_4$) and evaporated to leave an oil (7.2 g). Distillation afforded 2-fluoroquinoline (6.5 g, 54%) as a pale yellow oil; b.p $^{30}$ 134–136° C. (lit., b.p$^{30}$ 133° C.); δ$_H$ (400 MHz; CDCl$_3$; Me$_4$Si) 7.05 ppm (1H, d d, J$_{H3,H4}$ 8.8, J$_{H3,F}$ 2.8, H-3), 7.51 (1H, d d d, J$_{H5,H6}$ 8.0, J$_{H6,H7}$ 6.8, J$_{H6,H8}$ 0.8, H-6), 7.71 (1H, d d d, J$_{H7,H8}$ 8.0, J$_{H6,H7}$ 7.6, J$_{H5,H7}$ 1.2, H-7), 7.81 (1H, d, J$_{H5,H6}$ 8.0, H-5), 7.94 (1H, d, J$_{H7,H8}$ 8.4, H-8), 8.20 (1H, d d, J$_{H3,H4}$=J$_{H4,F}$ 8.4, H-4); δ$_F$ (250 MHz; CDCl$_3$; Me$_4$Si) −63.2 ppm; δ$_C$ (100 MHz, CDCl$_3$, Me$_4$Si) 110.0 ppm (d, $^2$J 42.1, C-3), 126.1 (d, $^4$J 2.6, C-8), 126.8 (d, $^4$J 1.9, C-4a), 127.5 (s, C-6), 128.0 (d, $^5$J 1.2, C-5), 130.6 (d, $^5$J 0.8, C-7), 141.9 (d, $^3$J 9.9, C-4), 145.7 (d, $^3$j 16.7, C-8a), 161.1 (d $^1$J 240.5, C-2); m/z (E1+) 147 (M$^+$, 100%).

Example 10: Fluorination of 3-bromoquinoline without use of base

A solution containing 3-bromoquinoline (1.0 g, 4.8 mmol) and iodine (1.22 g, 4.8 mmol) in CF$_2$ClCFCl$_2$ (30 ml) was placed in a fluorination apparatus fitted with a drying tube filled with soda lime. Elemental fluorine (5 mmol) as a 10% mixture in dry nitrogen was then passed through the stirred solution using narrow bore PTFE tubing at ca. 15 ml/min. After the fluorine had been added the solution was poured into 10% aqueous sodium metaisulfite solution (30 ml) and extracted with dichloromethane. The organic extracts were dried and evaporated to a brown oil (0.92 g). GC/MS analysis showed a 43% conversion of starting material. Column chromatography on silica gel with dichloromethane as eluant gave 2-fluoro-3-bromoquinoline (0.35 g, 74%); m.p. 75°–76° C. (vacuum sublimation oil bath temp. 50° C./<1 mmHg) as white needles; R$_F$ 0.69 (CH$_2$Cl$_2$); (Found: C, 47.5; H, 2.1; N, 6.2. C$_9$H$_5$NBrF requires: C, 47.8; H, 2.2; N, 6.2%); δ$_H$ (400 MHz, CDCl$_3$, Me$_4$Si) 7.55 ppm (1H, d d, J$_{H5,H6}$=J$_{H6,H7}$ 8.0, H-6), 7.74 (1H, d d d, J$_{H7,H8}$ 8.4, J$_{H6,H7}$ 7.2, J$_{H5,H7}$ 1.2, H-7), 7.76 (1H, d, J$_{H5,H6}$ 8.0, H-5), 7.91 (1H, d d, J$_{H7,H8}$ 8.4, J$_{H6,H8}$ 0.8, H-8), 8.42 (1H, d, J$_{H4,F}$ 8.4, H-4); δ$_C$ (100 MHz, CDCl$_3$, Me$_4$Si) 104.0 (d, $^2$J 43.2, C-3), 126.6 (s, C-6), 127.0 (d, $^4$J 2.7, C-8), 128.0 (d, $^5$J 1.9, C-5) 128.0 (d, $^4$J 2.2, C-4a), 130.9 (d, $^5$J 1.1, C-7), 143.5 (d,$^3$J 3.7, C-4), 144.2 (d, $^3$J15.1, C-8a), 157.3 (d $^1$J 238.1, C-2); δ$_F$ (235 MHz, CDCl$_3$, CFCl$_3$) −60.8 ppm (s); m/z (E1+) 225 (M$^+$, 100%), 227 (M$^+$, 74), 146 (56), 126 (23), 101 (18), 75 (14).

Example 11: Fluorination of 4-chloro-7-trifluoromethylquinoline

A solution containing 4-chloro-7-trifluoromethyl-quinoline (1.0 g, 4.3 mmol) and iodine (1.1 g, 4.3 mmol in CF$_2$ClCFCl$_2$ (30 ml) was placed in a fluorination apparatus fitted with a drying tube filled with soda lime. Elemental fluorine (5 mmol) as a 10% mixture in dry nitrogen was then passed through the stirred solution using narrow bore PTFE tubing at ca. 15 ml/min. After the fluorine had been added the solution was poured into 10% aqueous sodium metablsuifite solution (30 ml), neutralised with solid sodium bicarbonate and extracted with dichloromethane. The organic extracts were dried and evaporated to a yellow solid (1.09 g). GC/MS analysis showed a 5% conversion of starting material. Column chromatography on silica gel with dichloromethane as eluant gave 2-fluoro-4-chloro-7-trifluoromethyl-quinoline (0.05 g, 86%); m.p. 94°–95° C. (vacuum sublimation oil bath temp. 50° C./<1 mmHg) as white needles; R$_F$ 0.69 (CH$_2$Cl$_2$); (Found C, 47.7; H, 1.3; N, 5.5. C$_{10}$H$_4$NClF$_4$ requires; C, 48.1; H, 1.6; N, 5.6%); δ$_H$ (400 MHz, CDCl$_3$, Me$_4$Si) 7.32 ppm (1H, d, J$_{H,F}$ 2.4, H-3), 7.79 (1H, d d, J$_{H5,H6}$ 8.8, J$_{H6,H8}$ 1.6, H-6), 8.23 (1H, m, H-8), 8.32 (1H, d, J$_{H5,H6}$ 8.8, H-5); δ$_C$ (50 MHz, CDCl$_3$, Me$_4$Si) 112.3 ppm (d, $^2$J$_{CF}$ 45.5, C-2), 122.9 (m, C-6), 123,4 (q, $^1$J$_{CF}$ 272.7, CF$_3$), 125.6 (s, C-5), 126.2 (m, C-8), 126.7 (s, C-4a), 133.4 (q, $^2$J$_{CF}$ 33.2, C-7), 145.2 (d, $^3$J$_{CF}$ 18.7, C-8a), 146.7 (d, $^3$J$_{CF}$ 12.9, C-4), 160.9 (d, $^1$J$_{CF}$ 245.3, C-2); δ$_F$ (235 MHz, CDCl$_3$, CFCl$_3$) -55.0 ppm (1F, s, F-2), −59.2 (3F, s, CF$_3$); m/z (E1$^+$) 249 (M$^+$, 100%), 251 (M$^+$, 33), 230 (26), 214 (18), 201 (11), 199 (33), 194 (12), 145(26), 99 (19).

Example 12: Fluorination of Phenanthridine without use of base

A solution containing phenanthridine (1.0 g, 5.6 mmol) and iodine (1.4 g, 5.6 mmol) in CF$_2$ClCFCl$_2$ (30 ml) was placed in a fluorination apparatus fitted with a drying tube filled with soda lime. Elemental fluorine (7 mmol) as a 10% mixture in dry nitrogen was then passed through the stirred solution using narrow bore PTFE tubing at ca. 15 ml/min. After the fluorine had been added the solution was poured into 10% aqueous sodium metabisulfite solution (30 ml) and extracted with dichloromethane. The organic extracts were dried and evaporated to an orange oil (0.91 g). GC/MS analysis showed a 17% conversion of starting material. Column chromatography on silica get with dichloromethane as eluant gave 6-fluoro-phenanthridine (0.09 g, 48%); R$_F$ 0.78 (CH$_2$Cl$_2$); δ$_H$ (400 MHz, CDCl$_3$, Me$_4$Si) 7.61 ppm (1H, d d d, J$_{H1,H2}$=J$_{H2,H3}$=7.8, J$_{H2,H4}$ 1.2, H-2), 7.69 (2H, m, H-3 and H-9), 7.88 (1H, d d d, J$_{H7,H8}$ 8.4, J$_{H8,H9}$ 7.2, J$_{H8,H10}$ 1.4, H-8), 7.97 (1H, d d, J$_{H3,H4}$ 8.0, J$_{H2,H4}$ 1.2, H-4), 8.21 (1H, d d, J$_{H9,H10}$ 8.0, J$_{H8,H10}$ 1.4, H-10 8.45 (1H, d d, J$_{H1,H2}$ 8.0, J$_{H1,H3}$ 0.8, H-1), 8.52 (1H, d d, J$_{H7,H8}$ 8.4, J$_{H7,H9}$ 1.2, H-7); δ$_F$ (376 MHz. CDCl$_3$, CFCl$_3$) −68.2 ppm (s); δ$_C$ (100 MHz, CDCl$_3$, Me$_4$Sl) 117.3 ppm (d, J 35.1,C-6a), 122.2 (d, $^3$J 3.8, C-7), 122.2 (s, C-1), 123.9 (d, $^4$J 1.9, C-10b), 124.2 (s, C-10), 126.5 (d, $^6$J 2.3, C-2), 127.9 (s, C-9), 128.7 (d, $^4$J 1.6, C-4), 129.4 (s, C-3), 132.1 (s, C-8), 136.5 (d, $^3$J 7.2, C-10a), 141.5 (d, $^3$J 17.9, C-4a), 158.1 (d, $^1$J 248.7, C-6); m/z (E1$^+$) 197 (M$^+$, 100%).

Example 13: Fluorination of quinoxaline

A solution containing quinoxaline (15.6 g), 120 mmol) and iodine (30.5 g, 120 mmol) in CF$_2$ClCFCl$_2$ (150 ml) was placed in a fluorination apparatus fitted with a drying tube filled with soda lime. Elemental fluorine (165 mmol) as a 10% mixture in nitrogen was then passed through the stirred solution using narrow bore PTFE tubing at ca. 40 ml/min. After the fluorine had been added the solution was poured into 10% aqueous sodium metabisulfit solution (300 ml), neutralised with sodium bicarbonate and continuously extracted with dichloromethane for 24 hours. The organic extracts were dried and evaporated to an oil (13.6 g). GC/MS analysis showed a 49% conversion of quinoxaline. The oil was purified by column chromatography on silica gel using dichloromethane as eluant to give pure 2-fluoroquinoxaline as a pale yellow oil (5.30 g, 62% based on 49% conversion); $R_F$ 0.53; $\delta_H$ (200 MHz; CDCl$_3$; Me$_4$Si) 7.7 ppm (2H, m), 7.9 (1H, m), 8.1 (1H, m), 8.67 (1H, d, $J_{H,F}$ 7.9, H-3); $\delta_F$ (250 MHZ; CDCl$_3$; Me$_4$Si) -75.1 ppm (s); $\delta_C$ (50.3 MHz, CDC13, Me$_4$Si) 128.4 ppm (d, $^4J_{C,F}$ 1.6, C-8), 129.4 (s, C-7), 129.45 (s, C-6), 131.6 (s, C-5), 136.5 (d, $^2J_{C,F}$ 42.6, C-3), 139.72 (d, $^3J_{C,F}$ 10.9, C-8a), 141.52 (d $^4J_{C,F}$ 1.8, C-4a), 156.74 (d, $^1J_{C,F}$ 256.0, C-2); m/z (E1$^+$) 148 (M$^+$, 100), 129 (20), 121 (12), 103 (17), 76 (24), 50 (17); and 2,3-difluoroquinoxaline (0.27 g, 3%) as a pale yellow solid; $R_F$ 0.75; $\delta_H$ (400 MHz, CDCl$_3$, Me$_4$Si) 7.79 ppm (2H, m, Ar-H), 7.99 (2H, m, Ar-H); $\delta_C$ (50 MHz, CDCl$_3$, Me$_4$Si) 127.8 (s, C-8), 130.4 (s, C-7), 130.4 (s, C-7), 138.4 (d d, $^3J_{C,F}$ 5.4, C-4a), 146.1 (d d, $^1J_{C,F}$ 261.3,$^2J_{C,F}$ 39.5, C-2); $\delta_F$ (235 MHz, CDCl$_3$, CFCl$_3$) −82.8 ppm (s); m/z (E1+) 166 (M$^+$, 100%), 139 (11).

We claim:

1. A method of preparing a heterocyclic organic compound having at least one fluorine substitute in the heterocyclic ring, the method comprising reacting a heterocyclic compound with elemental fluorine in the presence of an elemental halogen other than fluorine. or in the presence of an interhalogen compound consisting of two different halogens.

2. The method according to claim 1 wherein the heterocyclic compound includes a five or six membered substituted or unsubstituted heterocyclic ring.

3. The method according to claim 1 wherein the heterocyclic compound includes a six-membered aromatic ring containing one or more nitrogen atoms.

4. The method according to claim 3 wherein the heterocyclic compound is pyridine, pyrimidine, pyridazine, pyrazine, triazine, quinoline, isoquinoline, quinoxaline, quinazoline or bipyridine.

5. The method according to claim 1 wherein the other halogen is selected from one or more of I$_2$, Br$_2$ and Cl$_2$.

6. The method according to claim 1 wherein the elemental fluorine is delivered to the heterocyclic compound in an inert gas.

7. The method according to claim 1 wherein the heterocyclic compound is contained in an organic solvent which also contains the other halogen, fluorine being passed into the organic solvent.

8. The method according to claim 7 wherein the organic solvent is a fluorinated organic solvent.

9. The method according to claim 1 wherein the heterocyclic compound is reacted with elemental fluorine in the presence of a base.

10. The method according to claim 9 wherein the base is triethylamine, tributylamine, N-methylpiperidine, sodium fluoride or potassium fluoride.

11. A method of preparing a heterocyclic organic compound having at least one fluorine substitute on the heterocyclic ring, the method comprising reacting a heterocyclic compound with elemental fluorine in the presence of one or more of I$_2$, Br$_2$, Cl$_2$, or an interhalogen compound consisting of two different halogens, wherein the heterocyclic compound is a five or six membered substituted or unsubstituted heterocyclic aromatic ring, and the reaction is performed in the presence of a base.

12. The method according to claim 3, wherein the ring is attached or benzofused to one or more other aromatic rings.

13. A product produced by the method of claim 1.

14. A product produced by the method of claim 11.

15. The method of claim 11, wherein the interhalogen compound is iodine monobromide or iodine monochloride.

16. The method of claim 1, wherein the method comprises preparing a heterocyclic organic compound having at least one fluorine substitute on a carbon atom in the heterocyclic ring.

* * * * *

UNITED STATES PATENT AND TRADEMARK OFFICE
CERTIFICATE OF CORRECTION

PATENT NO. : 5,859,255
DATED : January 12, 1999
INVENTOR(S) : Richard Dickinson Chambers, et al.

It is certified that error appears in the above-identified patent and that said Letters Patent is hereby corrected as shown below:

In column 1, line 31, delete "fluorodediazotisation. etc." and insert therefor --fluorodediazotisation, etc.--.

In column 2, line 20, delete "$CY_3{}^1$" and insert therefor --$CY^1{}_3$--.

In column 2, delete lines 30-32.

In column 3, delete lines 42-48.

In column 4, line 16, delete "E1 + " and insert therefor --$E1^+$--.

In column 4, line 18, delete "4.7" and insert therefor --4, 7--.

In column 4, line 35, delete "4.7" and insert therefor --4, 7--.

In column 4, line 61, delete "E1 + " and insert therefor --$E1^+$--.

In column 4, line 62, delete "$M^{30}+4$" and insert therefor --$M^+ + 4$--.

In column 5, line 24, delete "E1 + " and insert therefor --$E1^+$--.

In column 6, line 12, delete "$CDC1_3$" and insert therefor --$CDCl_3$--.

In column 6, line 13, delete "E1 + " and insert therefor --$E1^+$--.

In column 6, line 67, delete "$^4$JC-F" and insert therefor --$^4J_{C-F}$--.

In column 7, line 3, delete "$CFC1_3$)" and insert therefor --$CFCl_3$--.

In column 7, line 4, delete "(E1 +25" and insert therefor --$(E1^+)$ 125--.

UNITED STATES PATENT AND TRADEMARK OFFICE
CERTIFICATE OF CORRECTION

PATENT NO. : 5,859,255
DATED : January 12, 1999
INVENTOR(S) : Richard Dickinson Chambers, et al.

It is certified that error appears in the above-identified patent and that said Letters Patent is hereby corrected as shown below:

In column 7, line 26, delete "CDC1$_3$" and insert therefor --CDCl$_3$--.

In column 7, line 29, delete "$^3$j" and insert therefor --$^3$J--.

In column 7, line 42, delete "metaisulfite" and insert therefor --metabisulfite--.

In column 7, line 59, delete "(E1+)" and insert therefor --(E1$^+$) 125--.

In column 8, line 14, delete "C$_{10}$H$_4$NClF" and insert therefor --C$_{10}$H$_4$NClF$_4$--.

In column 8, line 47, delete "H-10" and insert therefor --H-10)--.

In column 8, line 50, delete "Me$_4$Sl" and insert therefor --Me$_4$Si--.

In column 8, line 50, delete "(d, J" and insert therefor --(d, $^2$J--.

In column 9, line 8, delete "250MHZ;" and insert therefor --250MHz;--.

In column 9, line 19, delete "(E1+)" and insert therefor --(E1$^+$) 125--.

In column 9, line 23, delete "in" and insert therefor --on--.

In column 9, line 26, delete "fluorine." and insert therefor --fluorine,--.

Signed and Sealed this

Sixteenth Day of May, 2000

Attest:

Q. TODD DICKINSON

Attesting Officer

Director of Patents and Trademarks